United States Patent
Ales, III

(10) Patent No.: US 7,449,614 B2
(45) Date of Patent: Nov. 11, 2008

(54) ABSORBENT ARTICLES INCLUDING A MONITORING SYSTEM POWERED BY AMBIENT ENERGY

(75) Inventor: Thomas M. Ales, III, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 42 days.

(21) Appl. No.: 11/512,794

(22) Filed: Aug. 29, 2006

(65) Prior Publication Data
US 2008/0058742 A1    Mar. 6, 2008

(51) Int. Cl.
*A61F 13/15*    (2006.01)
(52) U.S. Cl. .................. 604/361; 604/362; 604/367
(58) Field of Classification Search ............... 604/361, 604/362, 367
See application file for complete search history.

(56) References Cited

U.S. PATENT DOCUMENTS

| | | | |
|---|---|---|---|
| 3,199,095 A | 8/1965 | Hiroo | |
| 3,414,666 A | 12/1968 | Doundoulakis et al. | |
| 3,508,235 A | 4/1970 | Baisden | |
| 4,100,324 A | 7/1978 | Anderson et al. | |
| 4,522,897 A | 6/1985 | Walsh | |
| 4,704,116 A | 11/1987 | Enloe | |
| 4,748,366 A | 5/1988 | Taylor | |
| 4,753,088 A | 6/1988 | Harrison et al. | |
| 4,940,464 A | 7/1990 | Van Gompel et al. | |
| 5,098,771 A | 3/1992 | Friend | |
| 5,114,781 A | 5/1992 | Morman | |
| 5,116,662 A | 5/1992 | Morman | |
| 5,284,703 A | 2/1994 | Everhart et al. | |
| 5,350,624 A | 9/1994 | Georger et al. | |
| 5,371,326 A | 12/1994 | Clearwaters Dreager et al. | |
| 5,371,657 A | 12/1994 | Wiscombe | |
| 5,486,166 A | 1/1996 | Bishop et al. | |
| 5,490,846 A | 2/1996 | Ellis et al. | |
| 5,500,635 A | 3/1996 | Mott | |
| 5,508,684 A | 4/1996 | Becker | |
| 5,531,601 A | 7/1996 | Amoroso | |
| 5,575,554 A | 11/1996 | Guritz | |
| 5,645,542 A | 7/1997 | Anjur et al. | |
| 5,763,058 A | 6/1998 | Isen et al. | |
| 5,766,389 A | 6/1998 | Brandon et al. | |
| 5,796,345 A | 8/1998 | Leventis et al. | |
| 5,801,475 A | 9/1998 | Kimura | |
| 5,808,554 A | 9/1998 | Shuminov | |
| 5,820,973 A | 10/1998 | Dodge, II et al. | |
| 5,883,028 A | 3/1999 | Morman et al. | |
| 5,904,671 A | 5/1999 | Navot et al. | |

(Continued)

FOREIGN PATENT DOCUMENTS

EP    1 312 171 B1    3/2006

(Continued)

*Primary Examiner*—Jacqueline F. Stephens
(74) *Attorney, Agent, or Firm*—Randall W. Fieldhack

(57) ABSTRACT

Electrical monitoring devices may include alarm devices that are designed to assist parents or attendants in identifying a wet diaper condition shortly after the diaper has been soiled. The devices may produce a visual, an audible, or an electronic signal. These electrical monitoring devices have been powered by batteries, specifically small coin cell batteries. The power that is supplied by batteries dissipates over time requiring that the batteries be periodically replaced.

22 Claims, 7 Drawing Sheets

U.S. PATENT DOCUMENTS

| | | | |
|---|---|---|---|
| 5,931,764 A | 8/1999 | Freeman et al. | |
| 5,959,535 A | 9/1999 | Remsburg | |
| 5,964,743 A | 10/1999 | Abuto et al. | |
| 5,973,420 A | 10/1999 | Kaiserman et al. | |
| 6,025,783 A | 2/2000 | Steffens, Jr. | |
| 6,080,690 A | 6/2000 | Lebby et al. | |
| 6,097,607 A | 8/2000 | Carroll et al. | |
| 6,149,636 A * | 11/2000 | Roe et al. | 604/361 |
| 6,210,771 B1 | 4/2001 | Post et al. | |
| 6,231,557 B1 | 5/2001 | Krautkramer et al. | |
| 6,294,997 B1 | 9/2001 | Paratore et al. | |
| 6,362,389 B1 | 3/2002 | McDowall et al. | |
| 6,375,395 B1 | 4/2002 | Heintzeman | |
| 6,433,465 B1 | 8/2002 | McKnight et al. | |
| 6,493,933 B1 | 12/2002 | Post et al. | |
| 6,552,245 B1 | 4/2003 | Roessler et al. | |
| 6,580,013 B1 | 6/2003 | Belloso | |
| 6,641,134 B1 | 11/2003 | Dobbertin et al. | |
| 6,645,190 B1 | 11/2003 | Olson et al. | |
| 6,700,310 B2 | 3/2004 | Maue et al. | |
| 6,713,660 B1 * | 3/2004 | Roe et al. | 604/361 |
| 6,729,025 B2 | 5/2004 | Farrell et al. | |
| 6,737,789 B2 | 5/2004 | Radziemski et al. | |
| 6,774,800 B2 | 8/2004 | Friedman et al. | |
| 6,933,655 B2 | 8/2005 | Morrison et al. | |
| 6,958,443 B2 | 10/2005 | Stark et al. | |
| 7,005,778 B2 | 2/2006 | Pistor | |
| 7,019,241 B2 | 3/2006 | Grassl et al. | |
| 2006/0046907 A1 | 3/2006 | Rastegar et al. | |

FOREIGN PATENT DOCUMENTS

| | | |
|---|---|---|
| JP | 10/30998A A | 2/1989 |
| JP | 04/008361 A | 1/1992 |
| JP | 2000/140128 A | 5/2000 |
| WO | WO 00/37009 A2 | 6/2000 |
| WO | WO 00/52660 A1 | 9/2000 |
| WO | WO 02/16920 A2 | 2/2002 |
| WO | WO 02/061857 A1 | 8/2002 |
| WO | WO 02/078035 A1 | 10/2002 |
| WO | WO 02/095908 A1 | 11/2002 |
| WO | WO 03/015186 A2 | 2/2003 |
| WO | WO 03/034366 A1 | 4/2003 |
| WO | WO 03/041181 A2 | 5/2003 |
| WO | WO 03/051254 A2 | 6/2003 |
| WO | WO 03/063361 A1 | 7/2003 |
| WO | WO 03/096521 A2 | 11/2003 |
| WO | WO 2004/021944 A1 | 3/2004 |
| WO | WO 2004/034560 A2 | 4/2004 |
| WO | WO 2004/051786 A1 | 6/2004 |
| WO | WO 2004/054823 A1 | 7/2004 |
| WO | WO 2004/065908 A2 | 8/2004 |
| WO | WO 2004/091676 A1 | 10/2004 |
| WO | WO 2004/093300 A1 | 10/2004 |
| WO | WO 2005/062443 A1 | 7/2005 |
| WO | WO 2005/067840 A1 | 7/2005 |
| WO | WO 2005/103923 A2 | 11/2005 |
| WO | WO 2006/019818 A1 | 2/2006 |

* cited by examiner

ABSORBENT ARTICLES INCLUDING A MONITORING SYSTEM POWERED BY AMBIENT ENERGY

BACKGROUND

Almost all incontinence products sold today, including diapers, training pants, adult incontinence products, absorbent swimwear, and the like are manufactured to be disposed of after a single use. The absorbent articles typically contain a cover material, a liner, and an absorbent structure positioned between the cover material and the liner. The absorbent structure may include superabsorbent particles. Many absorbent articles are so efficient at absorbing liquids that it is sometimes difficult to ascertain whether or not the absorbent article has been insulted with a bodily fluid.

Accordingly, various types of electrical monitoring devices, such as moisture or wetness indicators, have been suggested for use in absorbent articles. The electrical monitoring devices may include alarm devices that are designed to assist parents or attendants in identifying a wet diaper condition shortly after the diaper has been soiled. The devices may produce a visual, an audible, or an electronic signal. These electrical monitoring devices have been powered by batteries, specifically small coin cell batteries. The power that is supplied by batteries dissipates over time requiring that the batteries be periodically replaced. A need therefore exists for an absorbent article having an electrical monitoring device that includes a source of electrical energy generated from ambient energy.

SUMMARY

In general, the present disclosure is directed to an absorbent article. For example, in one embodiment, the absorbent article includes an outer cover material, a liner, and an absorbent structure positioned between the outer cover material and the liner. Further, the absorbent article includes a monitoring system, where the monitoring system includes a current source that provides electrical energy from ambient energy.

Another version of the present invention includes an absorbent article having an outer cover material, a liner, and an absorbent structure positioned between the outer cover material and the liner. The absorbent article includes a monitoring system, where the monitoring system comprises a current source that provides electrical energy from ambient energy. The ambient energy being either a temperature gradient, motion, light, or vibration. The absorbent article also has an accumulator that accumulates an electric charge from the current source.

Finally, another version of the present invention includes an absorbent article having an outer cover material, a liner, and an absorbent structure positioned between the outer cover material and the liner. The absorbent article includes a monitoring system, wherein the monitoring system comprises a current source that provides electrical energy from ambient energy. The absorbent article also includes an accumulator that accumulates an electric charge from the current source. Further, the accumulator is a battery.

BRIEF DESCRIPTION OF THE DRAWINGS

Corresponding reference characters indicate corresponding parts throughout the drawings.

DETAILED DESCRIPTION

Figure 1:
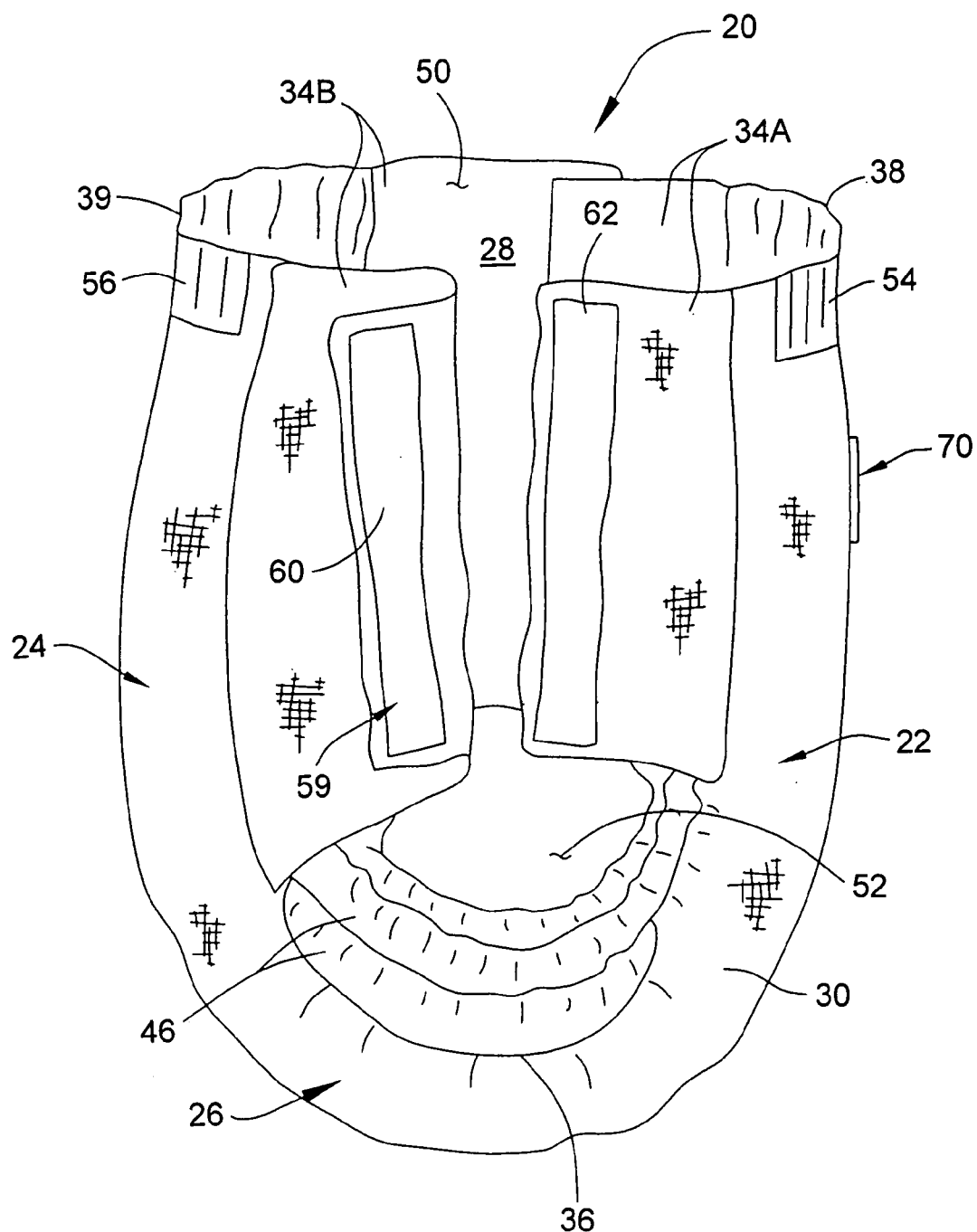
FIG. 1 is a side perspective of an article shown in the form of a pair of training pants having a mechanical fastening system fastened on one side of the training pants and unfastened on the opposite side thereof.

Referring now to the drawings and in particular to FIG. 1, an absorbent article is representatively illustrated therein in the form of children's toilet training pants and is indicated in its entirety by the reference numeral 20. The absorbent article 20 may or may not be disposable, which refers to articles that are intended to be discarded after a limited period of use instead of being laundered or otherwise conditioned for reuse. It is understood that the present invention is suitable for use with various other absorbent articles intended for personal wear, including but not limited to diapers, feminine hygiene products, incontinence products, medical garments, surgical pads and bandages, other personal care or health care garments, and the like without departing from the scope of the present invention.

By way of illustration only, various materials and methods for constructing training pants such as the pants 20, are disclosed in PCT Patent Application WO 00/37009 published Jun. 29, 2000, by A. Fletcher et al; U.S. Pat. No. 4,940,464 issued Jul. 10, 1990, to Van Gompel et al.; U.S. Pat. No. 5,766,389 issued Jun. 16, 1998, to Brandon et al., and U.S. Pat. No. 6,645,190 issued Nov. 11, 2003, to Olson et al. which are incorporated herein by reference.

Figure 4:
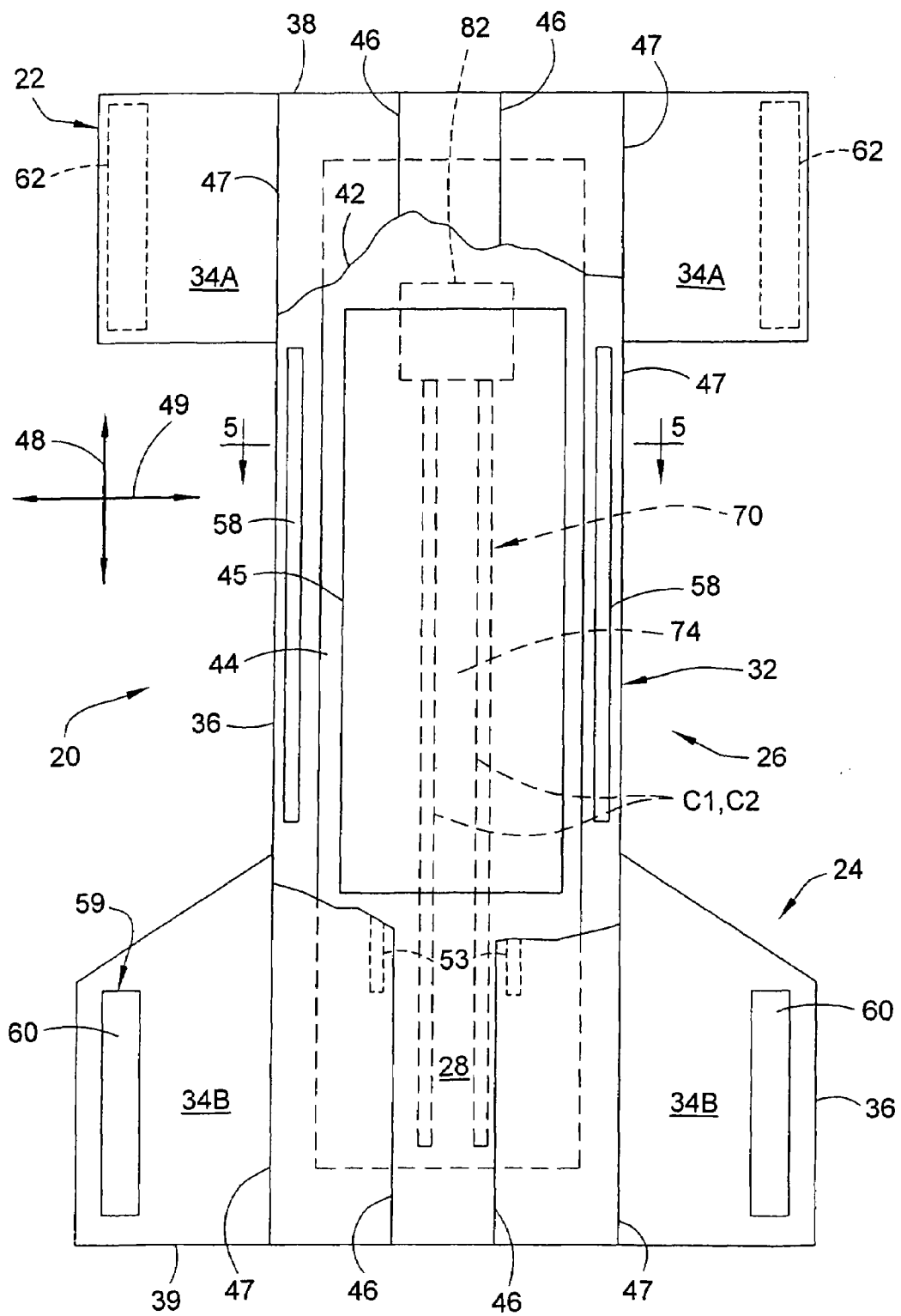
FIG. 4 is a top plan view of the training pants of FIG. 1 with the pants in an unfastened, unfolded, and laid flat condition, showing the surface of the training pants that faces the wearer when worn, with portions cut away to show underlying features.

The pair of training pants 20 is illustrated in FIG. 1 in a partially fastened condition. The pants 20 define a longitudinal direction 48 of the pants and a lateral direction 49 thereof perpendicular to the longitudinal direction as shown in FIG. 4. The pants 20 further define a pair of longitudinal end regions, otherwise referred to herein as a front waist region, generally indicated at 22, and a back waist region, generally indicated at 24, and a center region, otherwise referred to herein as a crotch region, generally indicated at 26, extending longitudinally between and interconnecting the front and back waist regions 22, 24. The front and back waist regions 22, 24 comprise those portions of the pants 20, which when worn, wholly or partially cover or encircle the waist or midlower torso of the wearer. The crotch region 26 generally is that portion of the pants 20 which, when worn, is positioned between the legs of the wearer and covers the lower torso and crotch of the wearer. The pants 20 also define an inner surface 28 that faces toward the wearer when the pants are being worn, and an outer surface 30 opposite the inner surface. With additional reference to FIG. 4, the pair of training pants 20 has a pair of laterally opposite side edges 36 and a pair of longitudinally opposite waist edges (broadly, longitudinal ends), respectively designated front waist edge 38 and back waist edge 39.

In the embodiment of FIGS. 1-4, the training pants 20 comprise a generally rectangular central absorbent assembly, generally indicated at 32, and side panels 34A, 34B formed separately from and secured to the central absorbent assembly. The side panels 34A, 34B are permanently bonded along seams to the central absorbent assembly 32 in the respective front and back waist regions 22 and 24 of the pants 20. More particularly, the front side panels 34A can be permanently bonded to and extend transversely outward beyond side margins 47 of the absorbent assembly 32 at the front waist region 22, and the back side panels 34B can be permanently bonded to and extend transversely outward beyond the side margins of the absorbent assembly at the back waist region 24. The side panels 34A and 34B may be bonded to the absorbent assembly 32 using attachment means known to those skilled in the art such as adhesive, thermal or ultrasonic bonding.

The front and back side panels 34A and 34B, upon wearing of the pants 20, thus comprise the portions of the training pants 20 which are positioned on the hips of the wearer. The front and back side panels 34A and 34B can be permanently bonded together to form the three-dimensional configuration of the pants 20, or be releasably connected with one another such as by a fastening system 59 of the illustrated aspects. As is known in the art, the side panels 34A, 34B may comprise elastic material or stretchable but inelastic materials.

Figure 2:
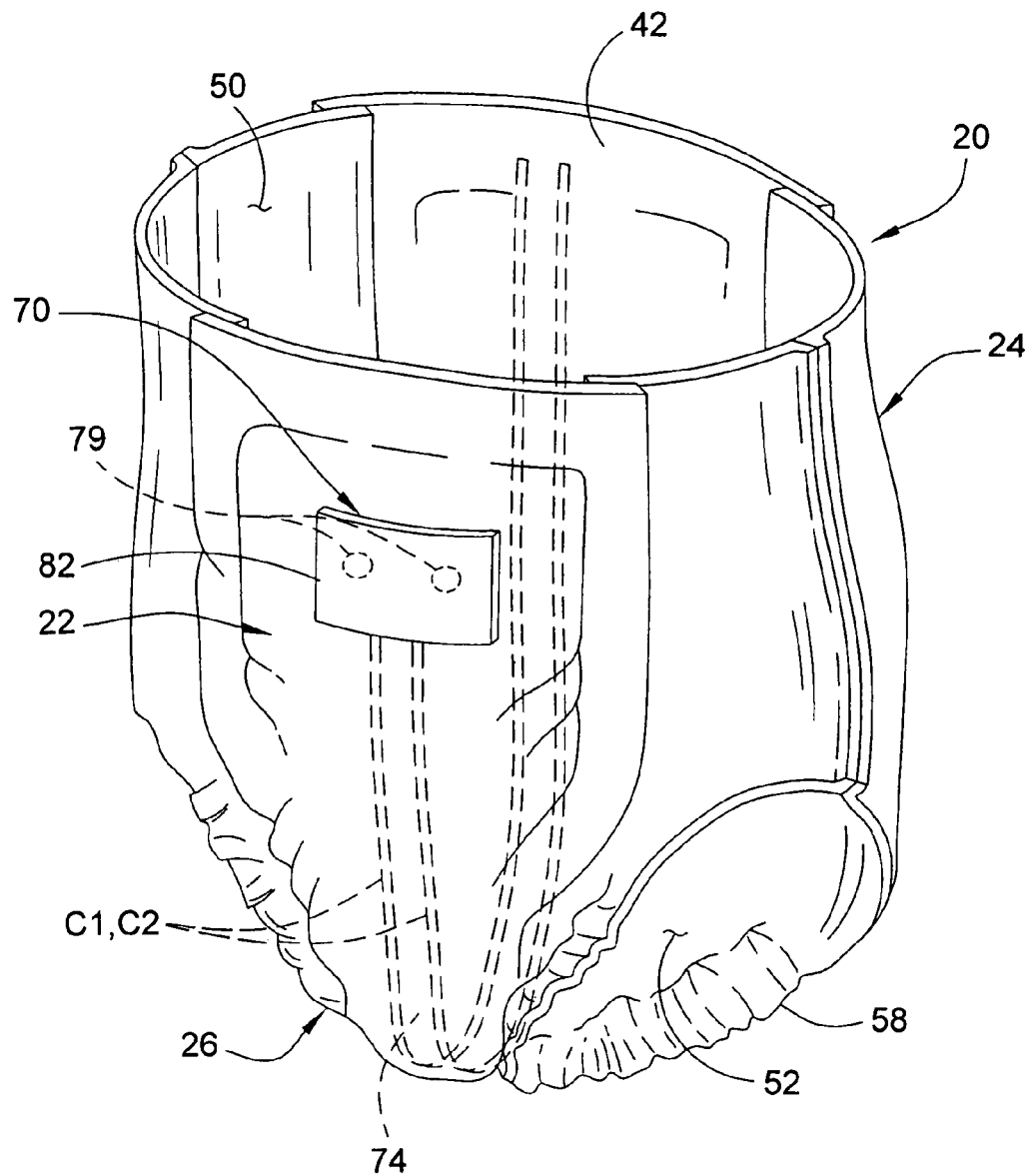
FIG. 2 is a perspective view of the pants of FIG. 1.
Figure 3:
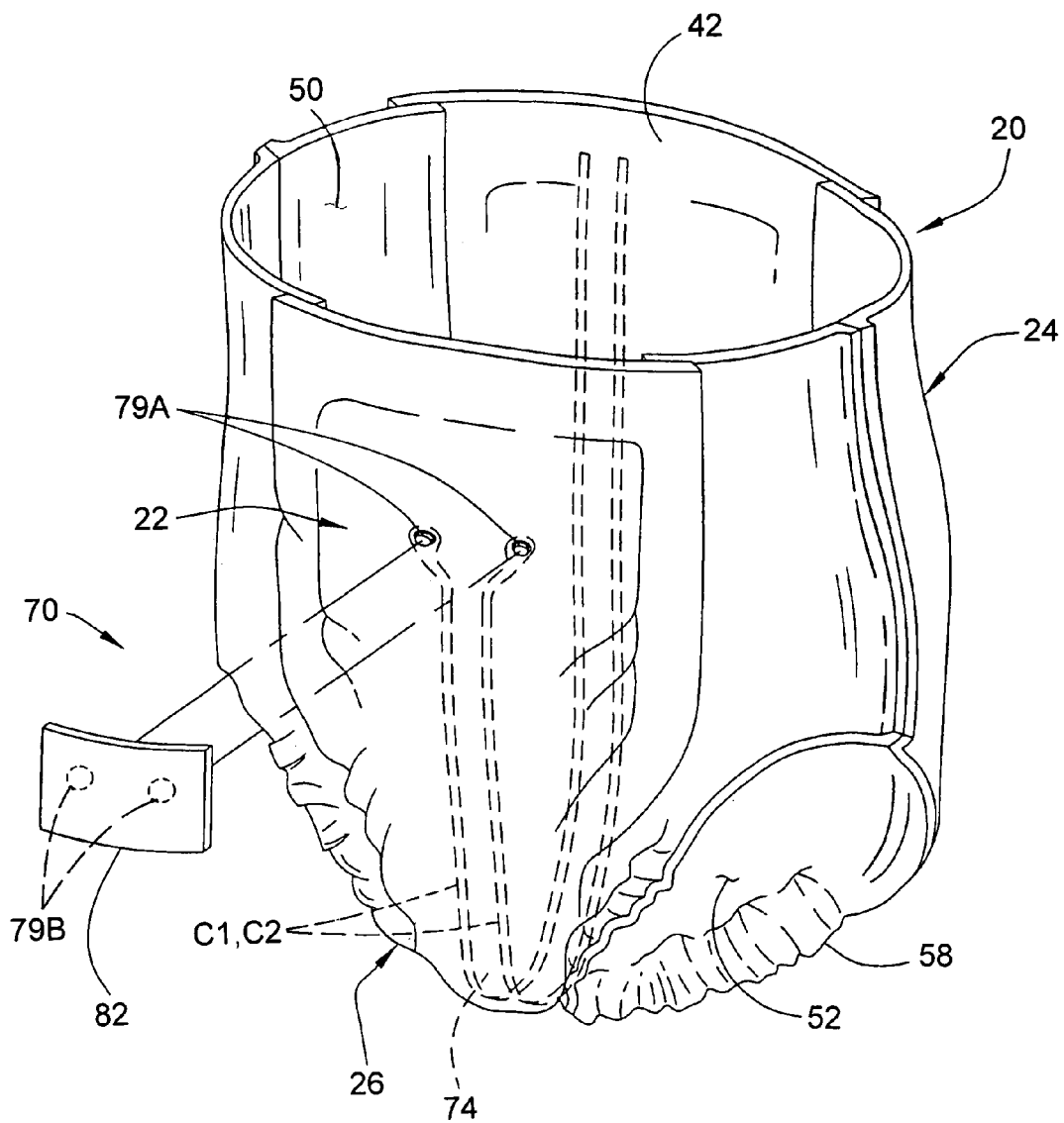
FIG. 3 is a perspective view of the pants similar to FIG. 2 showing a housing of a monitoring system removed from the article.

The absorbent assembly 32 is illustrated in FIGS. 1-3 as having a rectangular shape. However, it is contemplated that the absorbent assembly 32 may have other shapes (e.g., hourglass, T-shaped, I-shaped, and the like) without departing from the scope of this invention. It is also understood that the side panels 34A, 34B may instead be formed integrally with the absorbent assembly 32 without departing from the scope of this invention.

Figure 5:
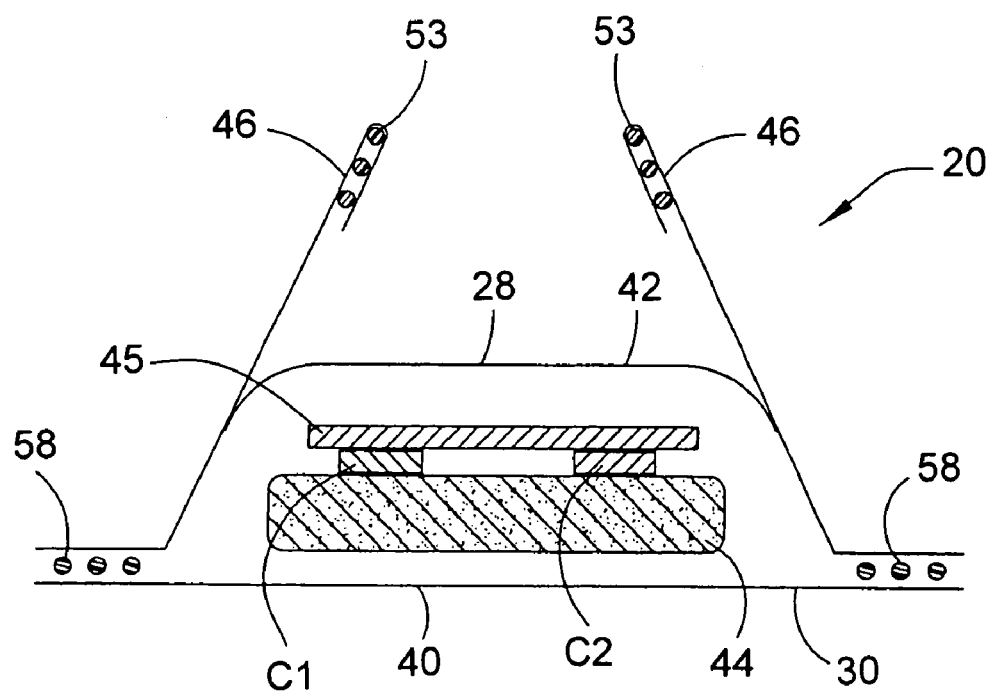
FIG. 5 is a cross-sectional view of the pants taken along the plane including line 5-5 of FIG. 4.

As shown best in FIGS. 4 and 5, the absorbent assembly 32 comprises an outer cover 40 and a bodyside liner 42 attached to the outer cover 40 in a superposed (opposed) relation therewith by adhesives, ultrasonic bonds, thermal bonds, pressure bonds, or other conventional techniques. The liner 42 is suitably joined to the outer cover 40 along at least a portion of the longitudinal ends of the pants 20. In addition, the liner 42 is suitably joined to the outer cover 40 along at least a portion of the lateral side edges of the pant 20. The liner 42 is suitably adapted, i.e., positioned relative to the other components of the pants 20, for a contiguous relationship with the wearer's skin during wear of the pants. The absorbent assembly 32 also comprises an absorbent structure 44 disposed between the outer cover 40 and the bodyside liner 42 for absorbing liquid body exudates released by the wearer and a surge management layer 45 disposed between the absorbent structure and the bodyside liner. A pair of containment flaps 46 is secured to the bodyside liner 42 for inhibiting the lateral flow of body exudates.

With the training pants 20 in the fastened position as partially illustrated in FIG. 1, the front and back waist regions are connected together by the fastening system 48 to define the three-dimensional pants configuration having a waist opening 50 and a pair of leg openings 52. The front and back waist edges 38 and 39 (e.g., longitudinal ends) of the training pants 20 are configured to encircle the waist of the wearer to define the waist opening 50 (FIG. 1) of the pants.

As illustrated in FIG. 4, a flap elastic member 53 can be operatively joined with each containment flap 46 in any suitable manner as is well known in the art. Suitable constructions and arrangements for the containment flaps 46 are generally well known to those skilled in the art and are described in U.S. Pat. No. 4,704,116 issued Nov. 3, 1987, to Enloe, which is incorporated herein by reference.

To further enhance containment and/or absorption of body exudates, the training pants 20 may comprise a front waist elastic member 54 (FIG. 1), a rear waist elastic member 56, and leg elastic members 58 (FIGS. 2-4), as are known to those skilled in the art. The flap elastic members 53, the waist elastic members 54 and 56, and the leg elastic members 58 can be formed of any suitable elastic material that is well known to those skilled in the art.

The fastening system 80 of the illustrated embodiment comprises laterally opposite first fastening components 60 adapted for refastenable engagement to corresponding laterally opposite second fastening components 62. In one embodiment, a front or outer surface of each of the fastening components 60, 62 comprise a plurality of engaging elements. The engaging elements of the first fastening components 60 are adapted to repeatedly engage and disengage corresponding engaging elements of the second fastening components 62 to releasably secure the pants 20 in its three-dimensional configuration. The fastening components 60, 62 can comprise any refastenable fasteners suitable for absorbent articles such as adhesive fasteners, cohesive fasteners, mechanical fasteners, or the like. Suitable fastening systems are also disclosed in the previously incorporated PCT Patent Application WO 00/37009 published Jun. 29, 2000, by A. Fletcher et al. and the previously incorporated U.S. Pat. No. 6,645,190 issued Nov. 11, 2003, to Olson et al.

The outer cover 40 suitably comprises a material that is substantially liquid impermeable. The outer cover 40 may comprise a single layer of liquid impermeable material, or more suitably comprise a multi-layered laminate structure in which at least one of the layers is liquid impermeable. While it is not a necessity for the outer layer to be liquid permeable, it is suitable that it provides a relatively cloth-like texture to the wearer. Alternatively, the outer cover 40 may comprise a woven or non-woven fibrous web layer that has been totally or partially constructed or treated to impart the desired levels of liquid impermeability to selected regions that are adjacent or proximate to the absorbent structure. The outer cover 40 may also be stretchable, and in some embodiments it may be elastomeric. Reference is made to U.S. Pat. No. 5,883,028, issued to Morman et al., U.S. Pat. No. 5,116,662 issued to Morman and U.S. Pat. No. 5,114,781 issued to Morman, all of which are hereby incorporated herein by reference, for additional information regarding suitable outer cover materials.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. The bodyside liner 42 may also be stretchable, and in some embodiments it may be elastomeric. Reference is made to U.S. patent application Ser. No. 09/563, 417 filed on May 3, 2000, by Roessler et al., U.S. patent application Ser. No. 09/698,512 filed on Oct. 27, 2000, by Vukos et al., both of which are incorporated by reference herein, for additional information regarding bodyside liner material.

The absorbent structure 44 is disposed between the outer cover 40 and the bodyside liner 42, which can be joined together by any suitable means such as adhesives, ultrasonic bonds, thermal bonds, or the like. While the illustrated absorbent structure 44 is shown and described herein as extending from the crotch region 26 into both the front and back waist regions 22 and 24, it is contemplated that the absorbent structure may extend from the crotch region into only the front waist region, or only the back waist region, without departing from the scope of this invention.

The absorbent structure 44 is suitably compressible, conformable, non-irritating to a wearer's skin, and capable of absorbing and retaining liquids and certain body wastes. For example, the absorbent structure 44 may comprise cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents, or the like, as well as combinations thereof.

The materials may be formed into an absorbent web structure by employing various conventional methods and techniques known in the art. For example, the absorbent structure 44 may be formed by a dry-forming technique, an air forming technique, a wet-forming technique, a foam-forming technique, or the like, as well as combinations thereof. Methods and apparatus for carrying out such techniques are well known in the art. The absorbent structure 44 may alternatively comprise a coform material such as the material disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference.

Superabsorbent material is suitably present in the absorbent structure 44 in an amount of from about 0 to about 90 weight percent based on total weight of the absorbent structure. The absorbent structure 44 may suitably have a density within the range of about 0.10 to about 0.35 grams per cubic centimeter. Superabsorbent materials are well known in the art and can be selected from natural, synthetic, and modified natural polymers and materials.

In one embodiment, the absorbent structure 44 may be stretchable so as not to inhibit the stretchability of other components to which the absorbent structure may be adhered, such as the outer cover 40 and bodyside liner 42. For example, the absorbent structure may comprise materials disclosed in U.S. Pat. Nos. 5,964,743; 5,645,542; 6,231,557; 6,362,389; and international patent application WO 03/051254, the disclosure of each of which is incorporated by reference herein.

The surge management layer 45 may be attached to various components of the article 20 such as the absorbent structure 44 and/or the bodyside liner 42 by methods known in the art, such as by adhesive, ultrasonic, or thermal bonding. The surge management layer 45 helps to decelerate and diffuse surges or gushes of liquid that may be rapidly introduced into the absorbent structure 44 of the article 20. Desirably, the surge management layer 45 can rapidly accept and temporarily hold the liquid prior to releasing the liquid into the storage or retention portions of the absorbent structure 44. Examples of suitable surge management layers 45 are described in U.S. Pat. Nos. 5,486,166 and 5,490,846. Other suitable surge management materials are described in U.S. Pat. No. 5,820,973. The entire disclosures of these patents are incorporated by reference herein.

Optionally, a substantially liquid permeable wrapsheet (not shown) may surround the absorbent structure 44 to help maintain the integrity of the absorbent structure 44.

The training pants 20 include a monitoring system that includes one or more sensors. The monitoring system may include sensors to indicate the presence of moisture or a bowel movement. The monitoring system may include a biosensor. The biosensor may be activated when contacted with an analyte contained in a body fluid. The analyte may be, for instance, a protein, a glycoprotein, an antibody, an antigen, hemoglobin, an enzyme, a metal salt, a hormone, or the like.

Healthcare products and incontinence products in caregiving institutions may include a monitoring system adapted to monitor humidity, temperature or a host of bio-indicators. In incontinence articles, for example, biosensors for a variety of disease conditions (e.g., cancer, diabetes, etc.) may be present and associated with respective warning indicators that are activated when a positive reading for a target analyte occurs. In one particular embodiment, the biosensor may be configured to sense a particular protein that would indicate a kidney problem. The monitoring system may also monitor the hydration level with a sensor quantifying the ionic strength of urine. Alternatively, the system may monitor sugar in urine or indicators for yeast in feminine care products.

Although the monitoring system may take on other configurations, this representative configuration of the system monitors an electrical characteristic of the pants and determines whether the child has urinated in the pants using such electrical characteristic. After detection of urine, the system may inform a caregiver and/or a child of the presence of the urine by generating an insult alarm. The alarm may be, for example, either an auditory signal, such as a song, or a tactile signal, such as temperature change, or a visual signal, such as a blinking light. It is understood that the system may comprise a device for sending a wireless signal to a remote auditory, visual, tactile or other sensory alarm.

In one particularly suitable embodiment, shown best in FIGS. 2-4, one example of the monitoring system is generally indicated by reference numeral 70. The monitoring system 70 includes a sensor for detecting the electrical property (e.g., resistance $\Omega$) of the article. The sensor includes a pair of spaced-apart generally parallel conductors C1, C2 disposed within the pants 20 that define a monitoring area 74 of the pants disposed between the conductors. The conductors C1, C2 may be constructed of any material that is generally electrically conductive. For example, the conductors may be constructed of metal strips (e.g., aluminum strips), metal films, coated films, conductive polymers, conductive inks, or conductive threads. Other conductors are within the scope of this invention. The conductors C1, C2 extend longitudinally from the front waist region 22, through the crotch region 26, to the back waist region 24 of the pants 20. As shown best in FIG. 5, the conductors C1, C2 are disposed within the absorbent assembly 32 between the absorbent structure 44 and the surge management layer 45, although the conductors may be disposed at other locations without departing from the scope of this invention.

Figure 6:
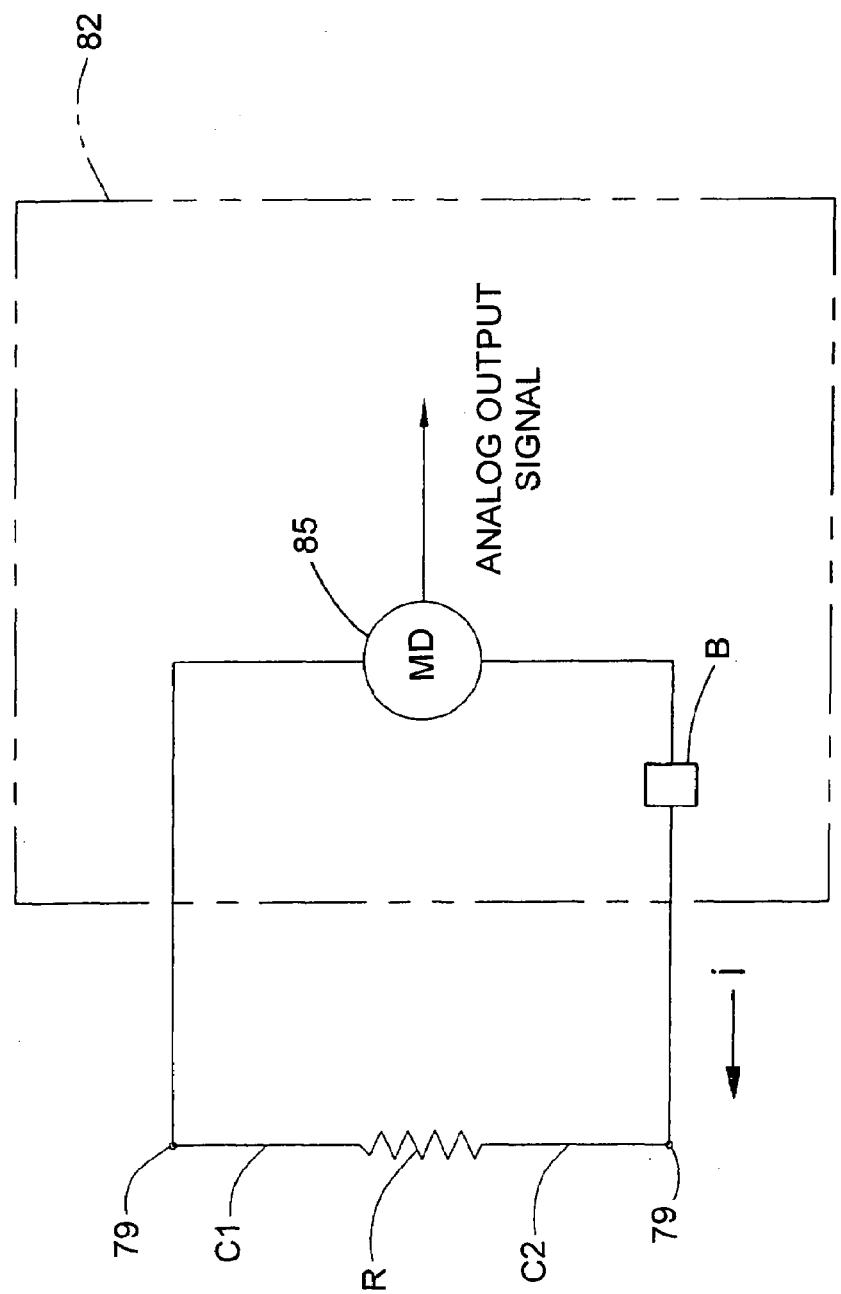
FIG. 6 is a schematic illustration of the pants and one embodiment of a monitoring system.

Current i from a current source B (illustrated schematically in FIG. 6) runs through the conductors C1, C2 of the sensor. The current source B may be a single current source, a plurality of current sources, or a combination of current sources and current accumulators as described below. The current source B may be a direct current source or an alternating current source. The current source B provides electrical energy for the monitoring system from ambient energy as described below. In the illustrated embodiment, the conductors C1, C2 are electrically connected to the current source by way of electrically conductive snap fasteners 79. Other ways of electrically connecting the conductors to the current source are within the scope of this invention. As illustrated in FIG. 3, each corresponding end of each conductor C1, C2 is connected to a first snap fastener member 79A located in the front waist region 22 of the pants 20. Alternatively, the first snap fastener member may be located in the back waist region 24, or other locations on the pants 20. A housing 82 that houses the current source B has corresponding second snap fastener elements 79B for engaging the first snap fasteners 79A and securing the housing to the pants 20. In addition to the current source B, the housing 82 of the present embodiment also houses the remaining components of the monitoring system 70 that will be described hereinafter, although it is contemplated that the housing may include only some or none of the remaining components. In the illustrated embodiment the housing 82 is releasably secured to the pants 20 by way of the snap fasteners 79, although it is understood that the housing may be permanently secured to the pants without departing from the scope of this invention.

A measuring device 85 (FIG. 6) of the sensor measures an electrical property of the monitoring area 74 of the pants 20. In one embodiment, the resistance R of the monitoring area 74 of the pants 20 is measured. Because the conductors C1, C2 are spaced apart, current from the current source B must pass through the monitoring area 74 to complete the circuit. As illustrated schematically in FIG. 6, the monitoring area 74 acts essentially as a resistor, as indicated by reference character R. When the monitoring area 74 is dry (e.g., before the presence of an insult), the resistance of the monitoring area is relatively high, for example, some resistance above 200 k$\Omega$. When the monitoring area 74 is wetted, its resistance drops, to some resistance less than 200 k$\Omega$ because of the electrically conductive nature of urine.

In another embodiment, the conductance of the monitoring area 74 of the pants 20 is measured. As stated above, urine is electrically conductive and the article 20 generally is not electrically conductive. Therefore, when the monitoring area 74 of the pants 20 is wetted, its conductance is greater than when it is dry. Other electrical properties of the pants 20, including impedance, may be measured without departing from the scope of this invention.

The measuring device 85 produces an analog output signal (FIG. 6) indicative of the electrical property of the monitoring area 74 of the pants 20. For example, the measuring device 85 can measure a resistance drop across the monitoring area 74, and produce an analog output signal corresponding to the resultant voltage drop. The output voltage signal can be used to determine other electrical properties, such as resistance or current, by performing suitable calculations known in the art or by using a reference table. For example, as is well known in the art, the voltage drop is indicative of the resistance of the pants when the current is constant. Thus, as explained below in further detail, the resistance of the pants 20 may be determined using the analog output signal of the measuring device 85.

In one embodiment, a percent difference test is conducted on the measured resistance of the pants 20 to determine the presence (or lack thereof) of an insult in the pants as the pants are being worn by the user. In this embodiment, a proportional difference (e.g., a percent difference) in the measured electrical property of the monitoring area of the pants over time is determined, and this proportional difference is compared with a difference threshold value to determine if an insult is present in the pants.

Figure 7:
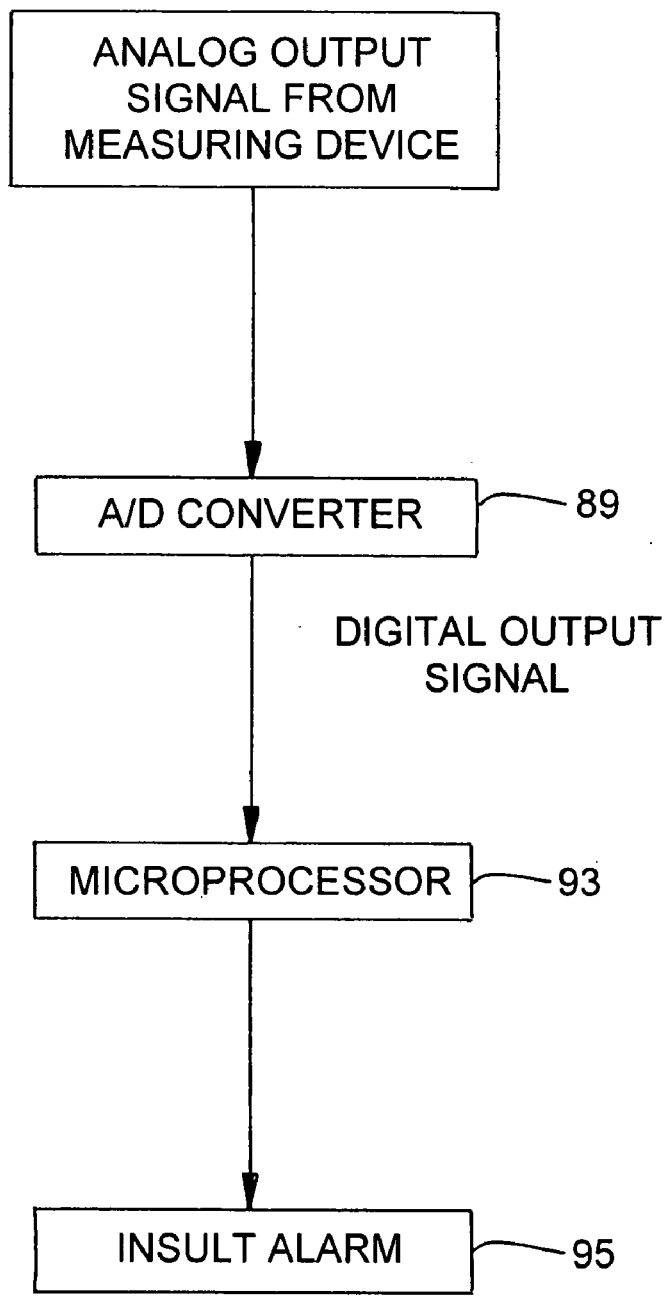
FIG. 7 is a block diagram for one embodiment illustrating an order of operation for components/devices, including a measuring device for measuring an electrical property of the pants and an analog-to-digital converter for converting an analog output from a measuring device into digital values to be read by a microprocessor.

In one example of this embodiment, illustrated in FIG. 7, an analog-to-digital converter 89 receives the analog output signal from the measuring device 85 and converts the signal into a digital output signal. A microprocessor 93 receives the digital output signal, which is representative of the magnitude of the electrical property (e.g., resistance) of the pants 20, and analyzes it to determine the presence of an insult. If the microprocessor 93 detects the presence of an insult, then it may activate the insult alarm 95. The analog-to-digital converter 89 is a conventional device for converting analog signals into digital signals that can be read by a microprocessor. The analog-to-digital converter 89 of the present embodiment may be a separate device or it may be a component of the microprocessor 93. For illustrative purposes, the electrical property will hereinafter be referred to as resistance although, as noted above, it may be any variable property of the garment which reflects wetness.

The sole current source B in traditional monitoring systems in absorbent articles has been batteries. The current that is supplied by batteries dissipates over time. As such, the traditional monitoring systems have had the disadvantage that either the batteries required changing, or in systems with batteries that couldn't be changed, the monitoring system had a limited life.

The monitoring systems of the present invention include a current source that provides electrical energy from ambient energy. Ambient energy is any energy that is generally present in the user's environment and is not directed to power electrical devices. Examples of ambient energy include motion, light, a temperature gradient, and vibration. The ambient energy may come from the user of the absorbent article. For example, the ambient energy may be motion from the user or a temperature gradient between the skin of the user and room temperature. The ambient energy may come from the environment that the user is in, for example the sun if the user is outdoors or electric lighting if the user is indoors.

A current source that provides electrical energy from ambient energy provides several benefits over a current source that dissipates over time. These benefits may include longer shelf life and longer usable life. These benefits are useful in the context of monitoring systems incorporated into absorbent articles.

A long shelf life may be particularly useful for absorbent articles used for toilet training. A caregiver may purchase a package of diapers or training pants having a monitoring system for the purpose of toilet training. If the user of the articles becomes toilet trained before the package of articles are depleted, there will be leftover articles. These articles may be disposed of, given to others, or perhaps saved for use on another child in the family. In this last instance, the articles may sit unused for months or, more likely, years. An absorbent article having a monitoring system including a current source that provides electrical energy from ambient energy provides a caregiver with confidence that the monitoring system will be useful for immediate use with a first child and for use in the future with a second child.

A long useable life is also useful in absorbent articles used for toilet training. The current source of the monitoring system may be included in a durable portion of the system that is designed to be moved from a first absorbent article to a second absorbent article. Some users in training may use this durable portion including the current source for many months, and perhaps more than a year. The life may be even longer if the durable portion of the system is then used by a subsequent user. A current source that provides electrical energy from ambient energy may theoretically power a monitoring system indefinitely, providing a consistent response. This consistent response may be critical in effective toilet training. A monitoring system that relies solely on battery power may provide an inconsistent response when the battery is depleted.

Many absorbent articles are designed to be fit near or around the waist and legs of a user. In addition, these articles may be designed to be as discrete as possible. A monitoring system incorporated into these articles would also be located near or around the waist and legs, and also be designed to be as discrete as possible. A monitoring system that provides electrical energy from ambient energy may be designed to provide additional functions beyond providing a current source. For example, in the case of electrostrictive polymers, the current source may also provide one or more elastic components to the absorbent article, for example waist elastic members 54, 56, leg elastic members 58, or flap elastic members 53. This multi-functional aspect may provide for a smaller, more discrete monitoring system.

As stated above, the ambient energy may be a temperature gradient. In this case, a thermoelectric generator takes advantage of a thermal gradient to generate a current according to the Seebeck effect. The thermoelectric generator may comprise a bottom plate, a top plate, and an array of foil segments. The array of foil segments is interposed between the bottom plate and the top plate in a side-by-side arrangement. Each of the foil segments is perpendicularly disposed between and in thermal contact with the bottom and top plates. A series of alternating n-type and p-type thermoelectric legs is disposed on a substrate of each one of the foil segments. The thermoelectric legs are generally fabricated from a bismuth telluride-type thermoelectric material, although any suitable material may be used. The top plate is disposed in spaced relation above the bottom plate.

The bottom and top plates may have a generally orthogonal configuration and may be fabricated from any rigid material such as ceramic material. The bottom plate and top plate are configured to provide thermal contact between a heat sink and a heat source such that a temperature gradient may be developed across the alternating n-type and p-type thermoelectric legs. The bottom plate may be thermally connected to the air surrounding a user and the top plate may be thermally connected to the skin of a user.

Each one of the foil segments may have a front substrate surface and a back substrate surface opposing the front substrate surface. The foil segments are arranged such that the back substrate surface of a foil segment faces the front substrate surface of an adjacent foil segment. The spaced, alternating n-type and p-type thermoelectric legs may be disposed in parallel arrangement to each other on the front substrate surface. Each of the n-type and p-type thermoelectric legs may be formed of a thermoelectric material generally having a thickness in the range of from about 5 microns ($\mu$m) to about 100 $\mu$m, with a preferable thickness of about 7 $\mu$m. The front substrate surface may have a surface roughness that is smoother than that of the back substrate surface in order to enhance the repeatability of forming the n-type and p-type thermoelectric legs on the front substrate surface.

A p-type and n-type thermoelectric leg pair makes up a thermocouple of the thermoelectric generator. The width of the thermoelectric legs may be in the range of from about 10 $\mu$m to about 100 $\mu$m. The length of the thermoelectric legs may be in the range of from about 100 $\mu$m to about 500 $\mu$m. A preferred length of the n-type and p-type thermoelectric legs is about 500 $\mu$m. A preferred width of the n-type thermoelectric leg is about 60 $\mu$m, while a preferred width of the p-type thermoelectric leg is about 40 $\mu$m. The geometry of the respective n-type and p-type thermoelectric legs may be adjusted to a certain extent depending on differences in the electrical conductivities of each n-type and p-type thermoelectric leg.

Alternatively, as stated above, the ambient energy source may be motion or vibration. In this case, a piezo-electric generator or electrostrictive polymer may take advantage of the motion or vibration to produce a current.

In the case of vibration, a piezo-electric generator may take advantage of a vibration to produce a current. In a piezo-electric generator, a pair of electrodes are provided on a piezo-electric plate. The piezo-electric plate moves when vibrated such that the piezo-electric plate is expanded or contracted during vibration. This expansion and contraction generates an AC voltage. Also a combination of vibration plates, orthogonal to one another, may be used so that the vibration can be divided two-dimensionally or three-dimensionally. This vibration may be caused by large movements of the user, for example walking or crawling, or by smaller movements of the wearer, for example breathing.

In the case of motion, a piezo-electric generator or an electrostrictive polymer may take advantage of the motion to produce a current. Electrostrictive (or synonymously, electroactive) polymers have been known to be used as low-mass actuators (artificial muscles). In one such artificial muscle application, a voltage is applied across the electrostrictive polymer via electrodes, causing the polymer to bend, stretch, or otherwise move or deform. The electrostrictive polymers can be dimensionally altered to a much greater extent than piezoelectric materials. This property of electrostrictive polymers may be used in reverse to harvest or generate electrical power from the general movement of objects such as from a human walking or crawling. As stated above, the electrostrictive polymers may comprise elastic elements of the absorbent article.

The polymer may be arranged in a variety of ways. Some candidate polymers for this application are, for example, polyacrylic acid, often referred to as PAA, and polyvinyl chloride (PVC). In addition, poly (3,3'-phthalidylidene-4,4'-biphenylylene), abbreviated PPB, is also a candidate electrostrictive polymer.

A promising polymer-electrode configuration for power generation, for example, is essentially a sandwich structure where polymer material and electrodes are interleaved. This combination of polymers between conductive sheets may be called ion-exchange polymer-metal composites or IPMCs for short.

The electrodes may be wired (hooked-up) in a "series" configuration. In this configuration, adjacent positive electrodes are attached to nearest neighbor negative electrodes. This series hook-up configuration for the interleaved electrodes permits the voltages generated across each polymer to be added, so that a relatively high ultimate output voltage is generated by the system. Alternatively, a parallel hook-up may be provided. In yet another configuration, combinations of series and parallel hook-ups are possible.

As stated above, the ambient energy may be light. In this case, a solar cell may take advantage of the light to produce a current. Solar cells may be comprised of semiconductor materials, such as silicon. In solar cells, a thin semiconductor wafer is specially treated to form an electric field, positive on one side and negative on the other. When light energy strikes the solar cell, electrons are knocked loose from the atoms in the semiconductor material. If electrical conductors are attached to the positive and negative sides, forming an electrical circuit, the electrons can be captured in the form of an electric current.

A photovoltaic module is a number of solar cells electrically connected to each other and mounted in a support structure or frame. Modules are designed to supply electricity at a certain voltage, such as a common 12-volt system. The current produced is directly dependent on how much light strikes the module.

An absorbent article having a monitoring system including a current source that provides electrical energy from ambient energy may utilize a single source of ambient energy. For example, the source may be a temperature gradient only utilizing a thermoelectric generator. Alternatively a plurality of sources of ambient energy may be utilized, for example a temperature gradient utilizing a thermoelectric generator and light utilizing a solar cell. This second configuration may be useful in situations when a single source may not provide a steady supply of current. In these situations, the multiple supplies of current may be chosen dependent upon the specific absorbent article and current demands of the monitoring system.

An absorbent article having a monitoring system including a current source that provides electrical energy from ambient energy may also include an accumulator that accumulates an electric charge from the current source. As stated above, the current sources that provide electrical energy from ambient energy may not provide a steady supply of electrical energy, therefore, an accumulator may be incorporated into the monitoring system. During periods when an excess amount of electrical energy is provided by ambient energy, the accumulator may store the excess electrical energy. The accumulator may then release the electrical energy during periods when a shortage of electrical energy is provided by ambient energy.

The accumulator may be any device adapted to accumulate, store, and release an electrical charge. The accumulator may store the electrical charge in any form, for example chemically, electrically, or mechanically. Suitable devices include batteries, capacitors, flywheels, and the like. A single accumulator may be used; alternatively, a plurality of similar or dissimilar accumulators may be used.

An absorbent article having a monitoring system including a current source that provides electrical energy from ambient energy may also include a second current source that provides electrical energy from non-ambient energy. This second source may be a battery. The second source may be an antenna that harvests tuned electromagnetic radio frequencies such as used in RFID devices. The second source may be a pair of electrodes that create a galvanic couple upon the addition of a conductive fluid, for example the addition of urine.

When introducing elements of the present invention or the embodiments thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

The invention claimed is:

1. An absorbent article comprising
an outer cover material;
a liner;
an absorbent structure positioned between the outer cover material and the liner; and
a monitoring system including a sensor, wherein the monitoring system is powered by a current source that converts ambient energy to electrical energy.

2. The absorbent article of claim 1 wherein the ambient energy is a temperature gradient.

3. The absorbent article of claim 1 wherein the ambient energy is motion.

4. The absorbent article of claim 1 wherein the ambient energy is light.

5. The absorbent article of claim 1 wherein the ambient energy is vibration.

6. The absorbent article of claim 1 wherein the current source is a thermoelectric generator.

7. The absorbent article of claim 1 wherein the current source is a piezo-electric generator.

8. The absorbent article of claim 1 wherein the current source is an electrostrictive polymer.

9. The absorbent article of claim 1 wherein the current source is a solar cell.

10. The absorbent article of claim 1 further comprising an accumulator that accumulates an electric charge from the current source.

11. The absorbent article of claim 10 wherein the accumulator is a battery.

12. The absorbent article of claim 10 wherein the accumulator is a capacitor.

13. The absorbent article of claim 1 further comprising a second current source that provides electrical energy from non-ambient energy.

14. The absorbent article of claim 13 wherein the second current source is a battery.

15. The absorbent article of claim 13 wherein the second current source is an antenna adapted to harvest tuned electromagnetic radio frequencies.

16. The absorbent article of claim 13 wherein the second current source is a pair of electrodes that require the addition of a conductive fluid to form a galvanic couple.

17. An absorbent article comprising
an outer cover material;
a liner;
an absorbent structure positioned between the outer cover material and the liner;
a monitoring system including a sensor, wherein the monitoring system is powered by a current source that converts ambient energy to electrical energy and the ambient energy is a temperature gradient, motion, light, or vibration; and
an accumulator that accumulates an electric charge from the current source.

18. The absorbent article of claim 17 wherein the current source is a thermoelectric generator.

19. The absorbent article of claim 17 wherein the current source is a piezo-electric generator.

20. The absorbent article of claim 17 wherein the current source is an electrostrictive polymer.

21. The absorbent article of claim 17 wherein the current source is a solar cell.

22. An absorbent article comprising
an outer cover material;
a liner;
an absorbent structure positioned between the outer cover material and the liner;
a monitoring system including a sensor, wherein the monitoring system is powered by a current source that converts ambient energy to electrical energy; and
an accumulator that accumulates an electric charge from the current source, wherein the accumulator is a battery.

* * * * *